United States Patent [19]

Hall-Jackson

[11] Patent Number: 5,780,798
[45] Date of Patent: Jul. 14, 1998

[54] BED OCCUPANT SENSING DEVICE

[76] Inventor: John Alan Hall-Jackson, Kirk Hammerton Hall, York, North Yorkshire Y05 8DA, United Kingdom

[21] Appl. No.: 698,116

[22] Filed: Aug. 15, 1996

Related U.S. Application Data

[63] Continuation of Ser. No. 399,759, Mar. 7, 1995, abandoned.

[30] Foreign Application Priority Data

| Mar. 9, 1994 | [GB] | United Kingdom | 9404531 |
| Dec. 8, 1994 | [GB] | United Kingdom | 9424735 |

[51] Int. Cl.⁶ .................................................... H01H 3/02
[52] U.S. Cl. ............................ 200/85 R; 128/782; 340/573; 340/666
[58] Field of Search ........................ 338/32 H; 307/119; 335/205–207; 340/573, 666, 667, 686; 200/333, 85 R, 85 A, 86 R; 73/65.01, 172; 128/774, 782, 714, 721

[56] References Cited

U.S. PATENT DOCUMENTS

| 4,020,482 | 4/1977 | Feldl | 200/85 R |
| 4,242,672 | 12/1980 | Gault |  |
| 4,263,586 | 4/1981 | Nicholas |  |
| 4,484,043 | 11/1984 | Musick et al. |  |
| 4,539,560 | 9/1985 | Fleck | 340/573 |
| 4,595,023 | 6/1986 | Bonnet |  |
| 4,633,237 | 12/1986 | Tucknot | 340/573 |
| 4,638,307 | 1/1987 | Swartout |  |
| 4,845,323 | 7/1989 | Beggs |  |
| 4,888,581 | 12/1989 | Guscott |  |
| 4,907,845 | 3/1990 | Wood |  |
| 4,951,032 | 8/1990 | Langsam |  |
| 5,410,297 | 4/1995 | Joseph et al. |  |

OTHER PUBLICATIONS

Medical Biological Engineering: Journal of the International federation for medical and biological engineering: vol. 8, No. 5, Sep. 1970, Stevenage (GB) A.H. Crisp et al. "The Design of a Motility Bed Including its Calibration for the Subject's Weight" pp. 456–458; Figures 1–3.

*Primary Examiner*—Gerald P. Tolin
*Attorney, Agent, or Firm*—Woodard, Emhardt, Naughton, Moriarty & McNett

[57] ABSTRACT

A sensing unit to be positioned between the matress of a bed and the bed frame for monitoring an occupant of the bed, the sensor consisting of thinly spaced upper and lower steel plates between which is located a point sensor such as a Hall effect transducer or a reed switch. The upper plate flexes in response to the weight of an occupant above. The sensing unit is to be attached to a control unit which generates an audible and visible alarm signal when the occupant leaves the bed. In a different embodiment, sensors are located in the bed frame to monitor the occupant of the bed.

1 Claim, 4 Drawing Sheets

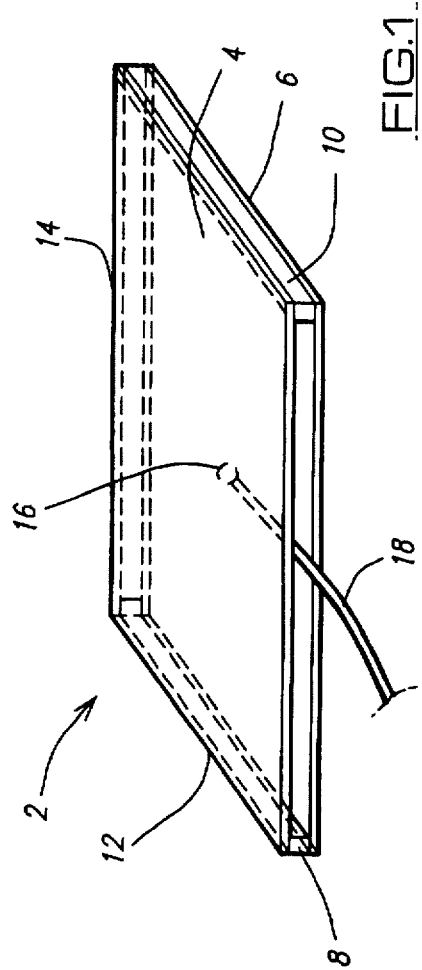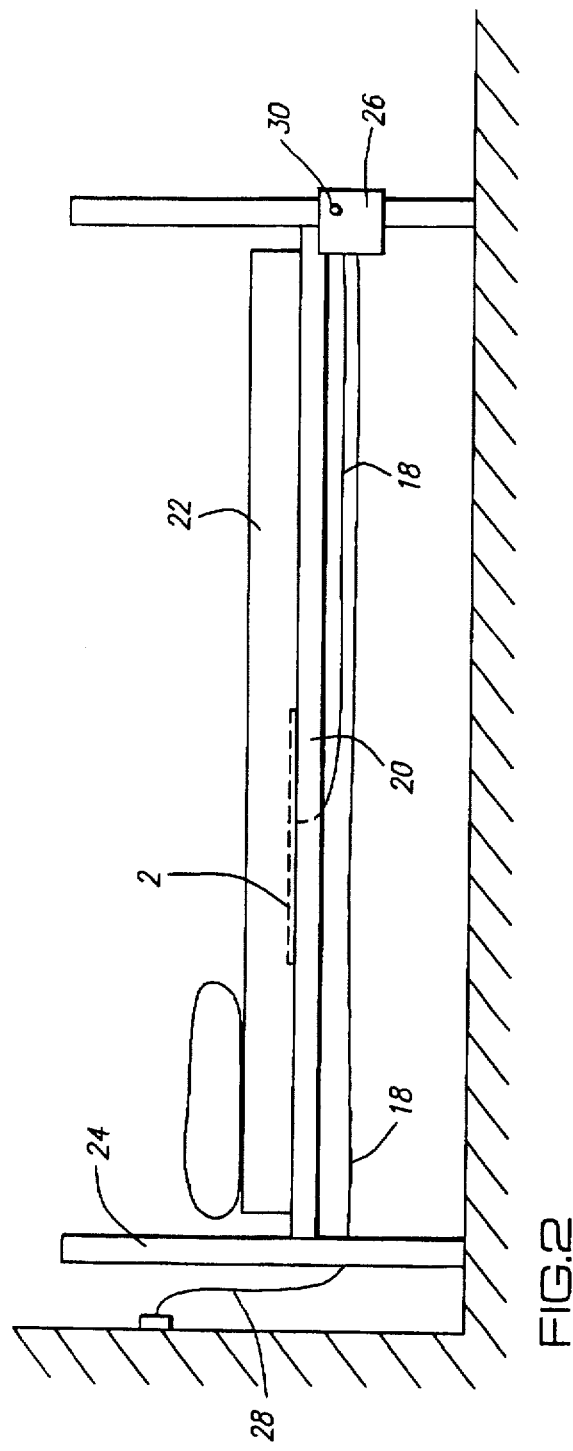

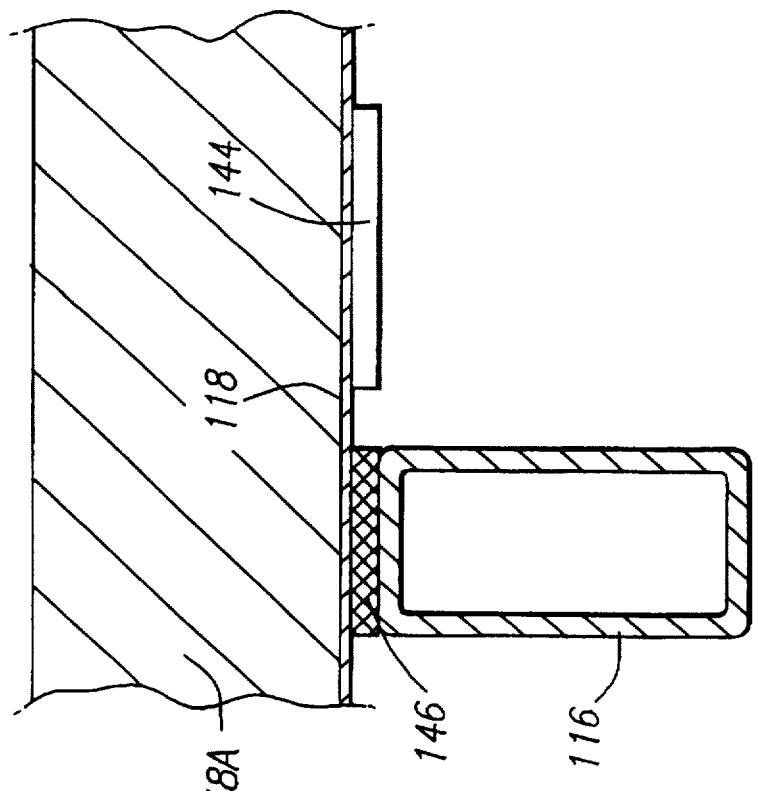
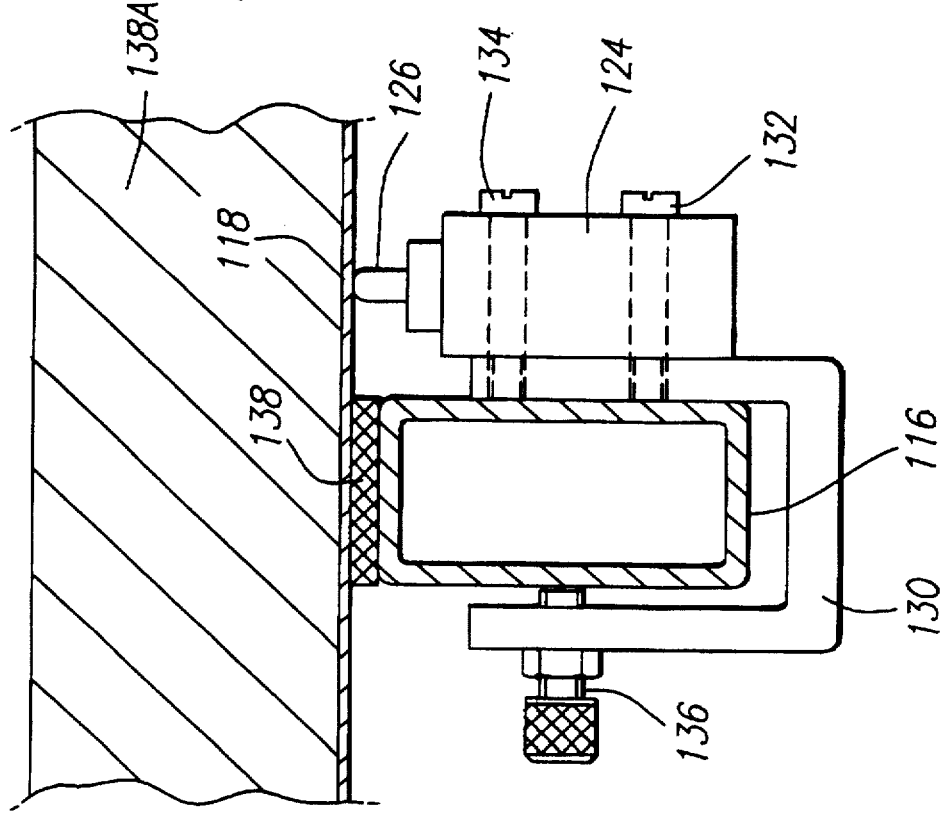

BED OCCUPANT SENSING DEVICE

This application is a continuation of application Ser. No. 08/399,759, filed Mar. 7, 1995, abandoned.

This invention relates to sensor arrangements, and in particular relates to sensor arrangements for beds which are for use mainly by persons who are unwell or infirm, and who require monitoring because of their condition.

Although the invention has particular application to beds having occupants to be monitored, it is to be mentioned that the invention can also be extended to items which may not strictly be termed beds, and such items include sofas and chairs, as long as such items are adapted to receive persons who are to be monitored. When the expression "beds" is used herein or is used in the singular, the said items are intended to be included within its meaning.

There have been proposed in various patent specifications different arrangements for monitoring the occupancy of a bed.

For example in U.S. Pat. No. 4,484,043 there is provided a weight responsive switching device in the form of a flexible and elongate sensor consisting of two flexible sheets cemented with electrically conductive layers, the conductive layers being spaced apart by an electrically insulating foam support frame. The sensor is placed across a mattress and a patient lies over the sensor to create electrical contact between the conductive layers. If a patient leaves or falls from the bed, the contact is broken and an alarm may be sounded to indicate a state of danger to the patient. However, the device is relatively fragile and is essentially a disposable item, requiring replacement on a monthly basis due to wear and tear.

A previous proposal was made in U.S. Pat. No. 4,295,133 which utilises a pair of flexible strips mounted to maintain parallelity between the strips even when flexed. A switching device is mounted inside the strips and is acted upon by an actuator located in a generally parallel relationship with the outer strips, which moves in response to flexing of the upper and lower strips together. The switch is to be placed below the mattress on which a patient lies. The device however requires resetting each time a patient leaves and reenters a bed. Furthermore, the device cannot be used when placed over a rigid surface. Since most hospital beds have a rigid frame over which the mattress is placed, the device is inutile for use in most hospitals.

The various detection and monitoring devices may be associated with alarms to signal critical condition.

The schemes which have been proposed have addressed the problem which exists in relation to bed ridden patients which is that often when such patients endeavour to leave the bed, they are so weak as not to be able to support themselves on their legs, and often fall to the floor to their considerable distress. However, these schemes have tended to be complicated and expensive.

It is an object of the invention to alleviate the drawbacks of the prior art monitoring systems.

In an extension of the basic concept of the invention, the system also provides a means of indicating movement of a patient in bed.

In accordance with the invention, there is provided a sensing device for monitoring an occupant of a bed, the sensing device comprising a substantially planar lower member, a substantially planar upper member being flexibly mounted in a spaced and generally parallel relation with the lower member, and a sensor responsive to changes in spacing between said members, characterised in that said sensor is a point sensor mounted to directly measure the spacing between the upper and lower members at a predetermined point, and said upper member is substantially rigid so that downward flexing of the upper member in an area of the upper member remote from said predetermined point causes downward flexing of the upper member at said predetermined point which is sensible by said sensor.

This arrangement provides for a sensing device which is able to monitor pressure exerted over a wide area on a bed whilst using a simple and effective point sensor arrangement.

The device is preferably adapted for use between the mattress and support frame of a bed. The lower member is preferably substantially rigid, which allows the sensing device to be placed on various types of support frames without affecting the operation of the device. For example, the support frame may be a plate or a meshwork metal grille.

The upper and/or the lower members are preferably metal plates, and are preferably of between 1 mm and 5 mm in thickness. The thickness of the plates is preferably 2 mm.

The upper and lower members are preferably spaced by less than 5 cm, and are further preferably spaced at around 1 cm apart, which provides for a compact and unobtrusive sensing unit.

The said members are preferably at least 20 cm wide.

The said sensor is preferably mounted centrally in the sensing device.

The upper and lower plates are preferably spaced by rigid mounting means located at opposed ends of the sensing unit, the sensor being located centrally of the said opposed ends. The said mounting means preferably comprise two parallel spaced bars, the said members being generally unsupported between the bars.

When positioned appropriately in a bed, the weight of an occupant on the sensing unit will cause the upper member to flex downwards. When the occupant leaves the bed, the upper member will flex upwards which movement is sensed by the sensor positioned between the plates.

The sensing unit is preferably coupled to an alarm indicator which is activated when an occupant leaves the bed in which the sensing unit is placed. The alarm may be an audible alarm so as to alert a nurse or other helper in the immediate viscinity. Furthermore, the unit may be connectable to the Nurse-Call systems operating in Hospitals so that the occupancy of a number of beds can be monitored by a single nurse at the Nurse-Call control desk.

The sensing unit is preferably coupled to a control unit responsive to the sensing unit which is provided with a light alarm such as a brightly flashing LED, the control unit being adapted to be mounted in a visible position on a bed. This provides for ready identification of a bed from which an occupant has departed or fallen.

Mere movement of the occupant from one part of the bed to another should not activate the alarm indicator for a prolonged period, although the sensing unit may be used to indicate when a patient approaches the periphery of the bed and is therefore in danger of falling from the bed.

The sensor may be a microswitch. However, the sensor preferably is of the type having two interactive parts, one part being mounted on each plate. For example the sensor may consist of a reed switch located on one member and a magnet on the other member. The sensor may consist of a Hall effect semiconductor device located on one member and a magnet on the other member. These sensors can be very small, being less than 1 cm in height, thus being ideal for use in the invention if appropriately positioned in the device.

In a particularly utile embodiment, the sensor is a linear output transducer such as a linear output Hall effect transducer, which allows for monitoring of lower levels of the occupants movement such as restlessness and tossing and turning. In this embodiment, the transducer when measuring and excessive drop in weight above the sensor may in any case trigger an alarm as described in relation to the above switching devices.

A restlessness monitor may also be provided by positioning two switching devices at opposed sides of the sensing unit. A patient tossing and turning from side to side will alternately activate both switches continually, which may be monitored using appropriate associated electronic circuitry.

According to a further independent aspect of the invention, a bed is provided with a support sheet which will when the bed is occupied by a patient be deflected to a predetermined degree, regardless of the position of the patient in the bed, and use is made of this deflection to operate a sensing means, which may be simply an on-off limit switch, or may be a weight responsive transducer positioned between the bed frame and the support sheet.

The sensing means may be positioned on a bed during manufacture of same or may be separately fitted on mountings attachable to the bed frame.

The present invention will now be described by way of example only with reference to the accompanying drawings, wherein:

FIG. 1 is an oblique view of a sensor unit according to one aspect of the present invention;

FIG. 2 is a plan view of the sensor unit of FIG. 1 when positioned in a bed for use;

FIG. 6 is a sectional side elevation of a detail showing an alternative method of mounting the micro switch;

FIG. 8 is a view similar to FIG. 6 but showing the use of a strain gauge.

Figure 3:
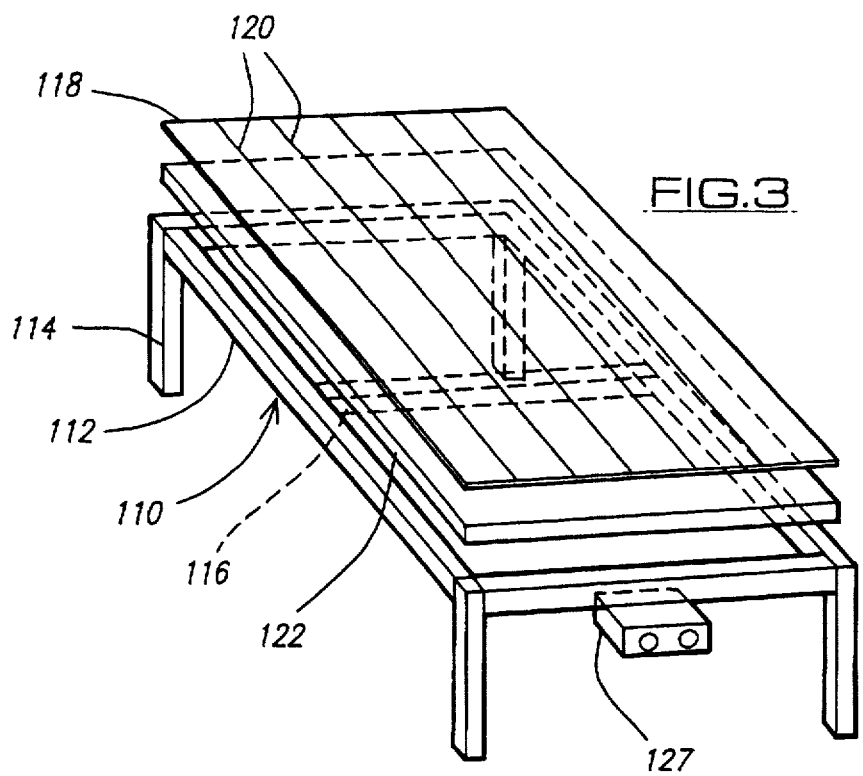
FIG. 3 is an exploded perspective view of a bed in accordance with a further aspect of the present invention.

Referring firstly to FIG. 1, a modified sensing unit 2 includes upper and lower thin but rigid steel plates 4 and 6. The plates 4 and 6 are each approximately 2 mm thick, and are rectangular having sides 12 and 14 measuring approximately 30 cm×60 cm. The plates are spaced approximately 10 mm apart by square sectioned metal bars 8 and 10. The spacers 8 and 10 are located in parallel relation along the periphery of the plates at the shorter ends of the plates 4 and 6. The sides of the plate are unsupported, allowing for flexing of the substantially rigid upper plate 4 to a shallow U-shaped section across its entire width.

A point sensor 16 is located between the plates, centrally of the spacer bars 8 and 10 and preferably in the geometric centre thereof, such that the sensor 16 senses vertical movement of the centre of the upper steel sheet or plate 4. Signals from the sensor 16 are sent to a control unit (shown in FIG. 2) via sensor cable 18.

As shown in FIG. 2, the sensor unit 2 is designed to be placed on a bed base 20, below a mattress 22, in a region towards the bedhead 24 of the bed region below the position where the buttocks of a patient rests if the patient lies at least generally centrally of the mattress. When a patient does lie on the mattress in that position, the upper plate 4 of the sensor unit flexes downwards, which movement is sensed by the sensor 16. The sensor is appropriately set so as to sense such a degree of movement of the upper plate 4 as is produced by the weight of a person, and also preferably is sensitive at least to the weight of a small or light person of 50–60 kg. Because the sides of the sensor are unsupported, and the rigidity of the upper plate 4, an occupant moving to one side of the bed will still cause flexing of the upper plate downwards which is sensible at the position of sensor 16. If the patient subsequently comes to lie dangerously close to the side of the mattress, or indeed leaves the mattress, the return movement of the upper plate 4 upwards is automatically sensed and a signal is passed via sensor cable 18 to control unit 26.

Control unit is provided with an audible alarm (not shown), a brightly flashing LED 30 and may also be provided with a lead 28 connecting the control unit to the patient port 32 of the Nurse-Call system in a Hospital or Care Home. The control unit 26 may furthermore be linked by radio wave transmission with portable receivers carried by caring staff. These receivers also alert the caring staff to a newly unoccupied bed, providing information as to the location of the bed on alert.

It will be appreciated that the sensing unit 2, having upper and lower housing sheets 4 and 6 protecting and operating the sensor 16 provides for a durable sensing unit 2. Furthermore, the unit is self-mounting insofar as the unit 2 is simply placed between the rigid bed base 20 and mattress 22. The sensing unit 2 may be utilised with the associated informational and alarm devices described in relation to the embodiments of FIGS. 3–8 below.

The sensor 16 may be a microswitch. However, the sensor preferably is of the type having two interactive parts, one part being mounted on each plate. For example the sensor may consist of a reed switch located on one member and a magnet on the other member. The sensor may consist of a Hall effect semiconductor device located on one member and a magnet on the other member. These sensors can be very small, being less than 1 cm in height, thus being ideal for use in the invention if appropriately positioned in the device.

It may be preferable to use a larger sensor, which would not fit within the 1 cm gap between the plates 4 and 6. In this case, the microswitch may be attached to the base of lower plate 6 with a portion projecting through an orifice in that plate so as to abut against the upper plate 4. This arrangement is particularly suitable where the bed base 20 consists of a metal meshwork supported on a frame. The exposed part of the sensor may then be placed between the meshwork when the sensing unit is placed on the bed base.

The sensor 16 may also be of the type giving a linear response, such as a linear output Hall Effect transducer which may be utilised to monitor lower levels of movement of the bed occupant. Restlessness could be charted by a recording device for inspection at a later time, for the purposes of assessing the need for medication or other attention. Should the patient leave the bed, the same device would trigger the alarm system via control unit 26.

The control unit 26 may also be connectable to a moisture detection device for monitoring the bed sheets of a patient lacking bowel control. The alarm system would be triggered on the detection of moisture to allow a nurse to rectify the matter, which would increase the overall level of comfort of the patient and reduce the incidence of bed sores.

Reverting to a further aspect of the invention, FIG. 3 shows a standard hospital bed 110 comprises a frame 112 standing on legs 114.

The frame 112 has one or more cross bars 116 extending between the longer sides, and normally the frame is covered by means of a metallic sheet 118 of the same rectangular configuration as the frame and sheet 118 is lightly ribbed as shown at 120 to improve its rigidity.

The sheet 118 is normally pop-riveted to the frame 112 which is made up of hollow rectangular sectioned bars. When such a bed is occupied by a patient, it flexes and/or is strained to such a degree that use can be made of the deflection and/or straining of the bed to provide a very simple and effective means of monitoring patient pressure or movement in the bed. In accordance with a suitable embodiment of this aspect of the invention, I propose that the sheet 118 be removed and that a sheet 122 of rubber or other compressible material of appropriate thickness be positioned on the frame 112 before the sheet 118 is replaced.

Additionally, in order that the bed can perform the function of the invention, a micro-switch sensor 124 having an operating button 126 is positioned on the centre of the cross bar 116 which is shown in FIG. 3, and which lies in the vicinity of the bed occupant's buttocks when the bed is properly occupied, and the micro switch is located in an aperture 126a in the sheet 122. The bed may have a junction control box 127 which is releasably clamped to the bottom of the bed frame where it cannot be reached by the patient. The box 127 may have an on/off switch to isolate same, a battery to power system, a battery run-down warning light and an audible alarm to respond locally to the bed occupants' movements. The box is electrically coupled to the micro switch to isolate same and it may have an on/off warning light.

Figure 4:
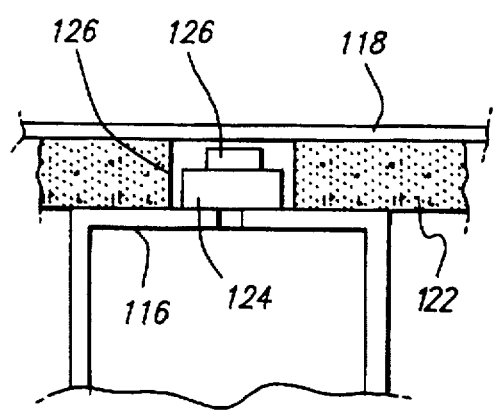
FIG. 4 is an enlarged sectional elevation showing the disposition of the micro switch in the arrangement of FIG. 3.
Figure 5:
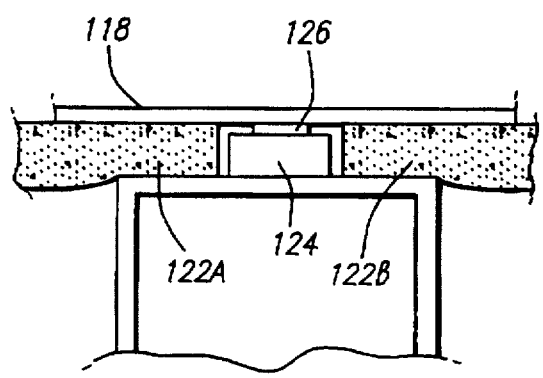
FIG. 5 is a view similar to FIG. 4 but showing the micro switch in the closed condition.

The arrangement shown in FIG. 4 is when the bed is not occupied, but when it is occupied, the sheet 118 will deflect as described herein, and as shown in FIG. 5 will compress the rubber sheet 122 in the regions 122A and 122B with the result that the deflecting sheet 118 will press button 126 of the micro switch and operate same to move it to its opposite condition. This condition will in fact be the monitoring condition so that when the micro switch is in the position of FIG. 5 it is closed and will break an alarm or monitoring circuit. When it is opened however as shown in FIG. 4, the alarm or monitoring circuit is complete and a signal will be given at a remote location to a person monitoring the occupant of the bed.

Thus, in normal operation the bed when occupied by a person will result in the micro switch 124 being in the circuit breaking condition, but should the person leave the bed, the sheet 118 will return to the FIG. 4 position by virtue of its own resilience and by virtue of the re-expansion of the rubber layer 122, and an alarm will be given or sounded so that a person monitoring a patient will know immediately that he or she has left the bed. Where such patient is of such fragileness and for example unable to walk, it is important that the person monitoring the patient should know as soon as he or she has left the bed.

It will be appreciated that the bed shown in FIG. 3 shows only the basic structure of the bed and it will of course be provided with a mattress and covering sheets and the like.

Figure 7:
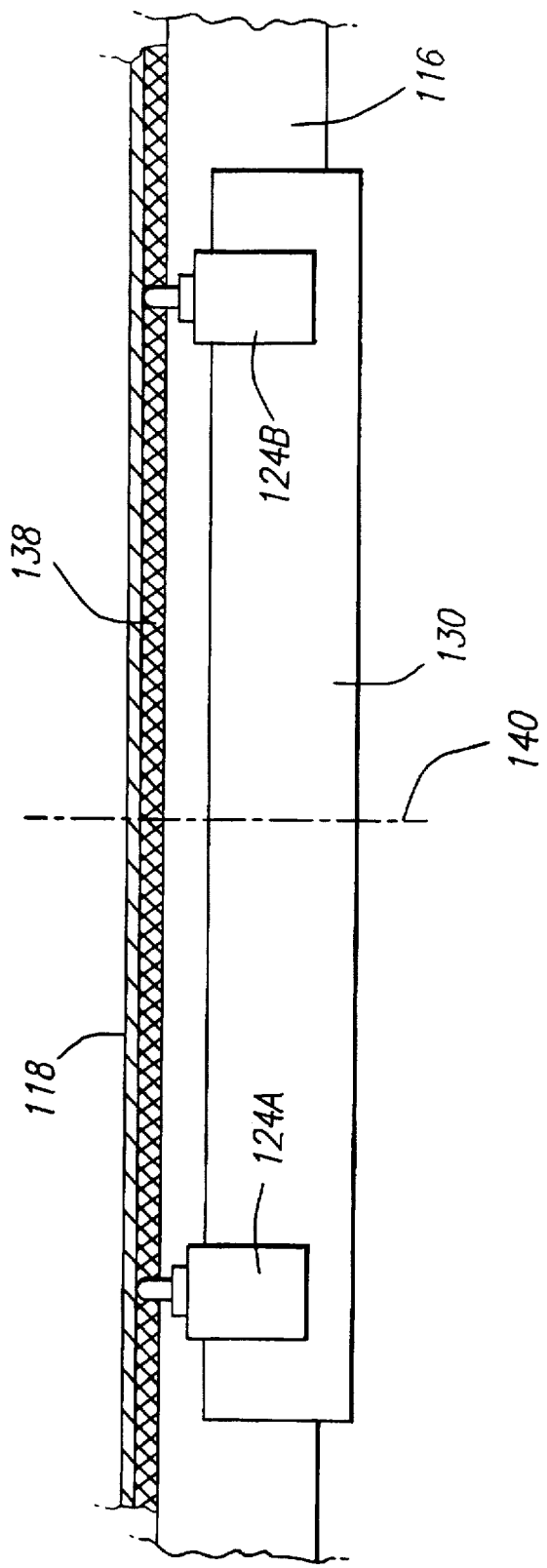
FIG. 7 is a sectional end elevation of an arrangement according to another embodiment of the further aspect of the invention.

FIGS. 6, 7 and 8 show modifications and/or alternative embodiments of the invention to indicate the range of applicability.

Referring to FIG. 6, this shows an arrangement wherein the micro switch 124 is attached to a U-shaped bracket 130 by means of a pair of screws 132, 134. The bracket 130 encircles the cross bar 116, and is clamped thereto by means of a clamping screw 136 which passes through the other limb of the bracket 116 and frictionally engages the wall of the cross bar 116 as shown.

It will be appreciated that the positioning of the micro switch is such that it will function in the same manner as described in relation to FIGS. 4 and 5. In this case, the compressible material is in the form of a strip 138 which simply overlies the top of the cross bar 116, and it is not necessary to provide a complete sheet of the compressible material as is provided for in the case of FIGS. 4 and 5.

By this arrangement, the micro switch can be connected to and removed from the cross bar 116 with the minimum of complication. Equally, the position of the micro switch vertically in relation to the cross bar 116 is easy to adjust, whereby the micro switch can be made to operate in the most efficacious manner. FIG. 6 also shows the sheet metal plate 118 and the micro switch operating plunger 126. A mattress 138A is also illustrated in this Figure, and it will be seen that it rests on plate 118.

In the arrangements so far described, only a single micro switch 124 is provided, but in accordance with the arrangement of FIG. 7 which is a sectional end view of the relevant components of the bed, the centre line of the bed is illustrated by reference 140, and again the cross bar 116 is clearly shown.

Two micro switches 124A and 124B are symmetrically arranged to opposite sides of the centre line 140, and the bracket 130 extends along the bar 116 for a sufficient length to enable a single bracket to receive both micro switches 124A and 124B. The bracket 130 is clamped to the cross bar 116 in the same manner as described in relation to FIG. 6 except that two or more clamping screws 136 may be provided. Indeed, the control box 127 which is shown in FIG. 3 and which preferably will be provided in each embodiment, is also clamped to the end rail of the bed frame by an arrangement similar to that illustrated in FIG. 6.

An advantage of the arrangement of FIG. 7 is that as two micro switches are used and are operated with the deflection of the sheet 118, the micro switches can be used not only for indicating when a patient is out of bed, but also when a patient is restless insofar as if the patient rolls to one side of the bed, the micro switch at the other side may be caused to change condition, and there will be one micro switch "on" and another "off". In such arrangement, at the remote indicating location, an appropriate lamp may be used to show such a condition. Such a lamp may for example have a green lens so that the person monitoring the patients will know that any particular patient is moving or is restless in bed and may need attention.

When both micro switches are in the open condition, i.e. the sheet 118 is deflected upwardly, then the person monitoring the patients will know that the patient in the appropriate bed has left his or her bed and can take corrective action.

It will be appreciated that an equivalent arrangement of switching sensors located at both sides of the sensing unit of FIGS. 1 and 2 could be used to equivalent effect.

The spacing between the micro switches 124A and 124B as shown in FIG. 7 may be in the order of 12 inches but clearly the most appropriate spacing can be selected, and the micro switches 124A and 124B are preferably adapted to be adjustably mounted along the bracket 130 in the direction of its length so that the spacing between the micro switches can be adjusted.

Again, an appropriate compressible strip 138 is provided between the cross bar 116 and the bed support sheet 118.

In each of the embodiments already described, the deflection of the sensing structure is sensed. However, when a patient is in bed, the whole bed structure is stressed, and according to other embodiments of the invention, sensors are used to detect the stressing of the bed structure. Thus, in the arrangement of FIG. 8, no micro switch is used but instead a strain gauge 144 is attached to the underside of the sheet 118 and this gauge will be stressed by virtue of stressing of the bed structure. Alternatively, the compress strip 146 may be replaced by an electronic load cell 146 sensing the weight incident upon the plate 118 located immediately above it. The change in stress or weight indicated by the load cell or strain gause can be used to operate the indicating means hereinbefore described.

Obviously when strain gauges or load cells are used, they can be positioned on the most appropriate locations of the bed structure.

Furthermore, it will be appreciated that the different types of sensors described above can be used interchangably. Where one type of sensor is described, any of the equivalents can be utilised at the same locations or in a suitable alternative location. It is however a common feature of all sensors used that the sensors are point sensors which sense changes in spacing or weight over only a small proportion of the area over which the weight of a patient is applied.

The invention provides cost-effective, hard wearing and reliable means for monitoring the occupant of a bed or the like. Other applications of the invention include the monitoring of the occupant of a lavatory seat by means of a sensor similar to that described in relation to bed occupancy, the sensor being located between the substantially rigid lavatory seat and the lavatory base.

It will be appreciated that various modifications and variants might be utilised by skilled persons without departing from the spirit nor exceeding the scope of the invention in its different aspects.

I claim:

1. A portable sensing device for placement in a bed to monitor the presence of an occupant in the bed, comprising:

(a) a rigid lower member having lower member ends, (b) a planar upper member in the form of a rigid plate having opposed sides and opposed ends which are respectively adjacent said lower member ends and which upper member is in spaced and generally parallel relation with the lower member, (c) a plurality of spacer means spacing the opposed ends of the plate with respect to the respective lower member ends but leaving a substantial portion of the opposed sides unsupported so that the center of the plate and its sides are free to flex relative to the support means under the weight of the occupant of the bed, (d) a sensor located between the plate and the lower member and centrally between the spacer means without contacting any of the plurality of spacer means so as to be sensitive to flexing of the plate under the weight of the occupant of the bed, and (e) said sensor comprising a limit switch or transducer actuated by the relative movement between said plate and said rigid lower member.

* * * * *